(12) United States Patent
Pulé et al.

(10) Patent No.: US 11,613,559 B2
(45) Date of Patent: Mar. 28, 2023

(54) NUCLEIC ACID CONSTRUCT

(71) Applicant: AUTOLUS LIMITED, London (GB)

(72) Inventors: Martin Pulé, London (GB); Shaun Cordoba, London (GB)

(73) Assignee: AUTOLUS LIMITED, London (GB)

( * ) Notice: Subject to any disclaimer, the term of this patent is extended or adjusted under 35 U.S.C. 154(b) by 0 days.

(21) Appl. No.: 15/568,862

(22) PCT Filed: Apr. 26, 2016

(86) PCT No.: PCT/GB2016/051165
§ 371 (c)(1),
(2) Date: Oct. 24, 2017

(87) PCT Pub. No.: WO2016/174409
PCT Pub. Date: Nov. 3, 2016

(65) Prior Publication Data
US 2018/0099994 A1 Apr. 12, 2018

(30) Foreign Application Priority Data

Apr. 27, 2015 (GB) ..................................... 1507108

(51) Int. Cl.
| | |
|---|---|
| *C07K 7/08* | (2006.01) |
| *C12N 5/0783* | (2010.01) |
| *C07K 16/28* | (2006.01) |
| *C07K 14/725* | (2006.01) |
| *C07K 14/705* | (2006.01) |
| *C07K 14/685* | (2006.01) |
| *C12N 9/16* | (2006.01) |

(52) U.S. Cl.
CPC .............. *C07K 7/08* (2013.01); *C07K 14/685* (2013.01); *C07K 14/7051* (2013.01); *C07K 14/70517* (2013.01); *C07K 14/70521* (2013.01); *C07K 14/70589* (2013.01); *C07K 16/2803* (2013.01); *C12N 5/0636* (2013.01); *C12N 9/16* (2013.01); *C12Y 301/03048* (2013.01); *C07K 2317/622* (2013.01); *C07K 2319/02* (2013.01); *C07K 2319/03* (2013.01); *C07K 2319/30* (2013.01); *C07K 2319/33* (2013.01); *C07K 2319/50* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,052,906 B1 | 5/2006 | Lawson et al. | |
| 8,361,744 B2* | 1/2013 | Marrichi | C12N 15/70 |
| | | | 435/71.1 |
| 2018/0100163 A1 | 4/2018 | Pule et al. | |

FOREIGN PATENT DOCUMENTS

| | | | | |
|---|---|---|---|---|
| CN | 103483452 A | 1/2014 | | |
| WO | WO-2007/014162 A2 | 2/2007 | | |
| WO | WO-2007014162 A2 * | 2/2007 | ............. | C07K 16/00 |
| WO | WO-2013/185552 A1 | 12/2013 | | |
| WO | WO-2013185552 A1 * | 12/2013 | ......... | C07K 16/3092 |
| WO | WO-2015/052538 A1 | 4/2015 | | |
| WO | WO-2015/075469 A1 | 5/2015 | | |
| WO | WO-2015075469 A1 * | 5/2015 | ............. | A61K 35/17 |

OTHER PUBLICATIONS

Wilkie et al Journal of Clinical Immunology, 1059-1070 (Year: 2012).*
Nagaraj, R Proc. Indian Acad Sci, 98, 479-485 (Year: 1987).*
Wilkie et al J Clin Immunol. 32:1059-1070 (Year: 2012).*
Hiller et al Nucleic Acids Res. W375-W379 (Year: 2004).*
Zhang et al J Gene Med7: 354-365 (Year: 2005).*
Gion et al(mAbs 5:4, 595-607; Jul./Aug. (Year: 2013).*
Humpreys et al Protein Expression and Purification 26 309-320 (Year: 2002).*
Haryadi et al PLoS Pne , 10(2) e0116878 , 1-16 (Year: 2015).*
Zhou et al Micro Cell Fact. 15, 47, 1-11 (Year: 2016).*
Simons et al Journal of Immunological methods 263, 133-147 (Year: 2002).*
Simons et al Nature Biotechnology, 14, 629-634 (Year: 1996).*
U.S. Appl. No. 15/568,859 (US-2018-0100163 A1), filed Oct. 24, 2017.
Donnelly et al., The 'cleavage' activities of foot-and-mouth disease virus 2A site-directed mutants and naturally occurring '2A-like' sequences, J. Gen. Virol., 82(Pt. 5):1027-41 (2001).
International Search Report and Written Opinion, dated Jul. 7, 2016. International Application No. PCT/GB2016/051165 corresponding to the present application U.S. Appl. No. 15/568,862.
Wilkie et al., Dual targeting of ErbB2 and MUC1 in breast cancer using chimeric antigen receptors engineered to provide complementary signaling, J. Clin. Immunol., 32(5):1059-70 (2012).
Hedge et al., "Combinational Targeting Offsets Antigen Escape and Enhances Effector Functions of Adoptively Transferred T Cells in Glioblastoma," Molecular Therapy 21(11):2087-2101 (2013).

* cited by examiner

*Primary Examiner* — Anoop K Singh
(74) *Attorney, Agent, or Firm* — Marshall, Gerstein & Borun LLP

(57) ABSTRACT

The present invention provides a nucleic acid construct comprising the following structure: A-X-B in which A is nucleic acid sequence encoding a first polypeptide which comprises a first signal peptide; B is nucleic acid sequence encoding a second polypeptide which comprises a second signal peptide and X is a nucleic acid sequence which encodes a cleavage site, wherein the first signal peptide or the second signal peptide comprises one or more mutation(s) such that it has fewer hydrophobic amino acids.

11 Claims, 7 Drawing Sheets

Specification includes a Sequence Listing.

NUCLEIC ACID CONSTRUCT

CROSS-REFERENCE TO RELATED APPLICATIONS

This application is a U.S. National Phase of International Application No. PCT/GB2016/051165 filed Apr. 26, 2016, which claims priority from Application 1507108.7 filed on Apr. 27, 2015 in the United Kingdom.

FIELD OF THE INVENTION

The present invention relates to constructs and approaches for modulating the relative expression of polypeptides co-expressed from a single vector. In particular, the invention relates to modulating the expression of a transmembrane protein co-expressed from a single vector with a second polypeptide.

BACKGROUND TO THE INVENTION

It is often desirable to express different proteins from the same vector since multiple transduction of the same cell is difficult, expensive and unpredictable. Different methods have therefore been developed to allow co-expression of two proteins from a single vector (see FIG. 1).

Initial attempts used two different promoters within the same cassette. This results in two separate transcripts each of which code for a separate protein. This is a difficult approach for a number of reasons. A key problem is "promoter interference" whereby one promoter dominates and causes silencing of the second promoter. In addition, different promoters work differently in different cellular contexts and this makes consistent "tuning" of the relative expression of each transgene difficult to achieve.

An alternative approach is to use an Internal Ribosome Entry sequence (IRES). Here, a single transcript is generated. The IRES sequence in the transcript is placed between the open reading frames for the two transgenes and mimics an mRNA cap structure. Hence, the ribosome either initiates translation at the 5' cap or the IRES resulting in expression of two separate proteins. A key limitation with this approach is the inability to control relative expression. The 3' transcript is typically expressed less than the 5' one, but the ratio of expression is difficult to predict and tune.

A further approach has been provided following characterization of the role of foot-and-mouth-disease virus (FMDV) 2A peptide in allowing FMDV (and related viruses) to express multiple proteins from a single open reading frame (ORF) (Donnelly et al; *J. Gen. Virol.*; 82, 1027-1041 (2001)). The 2A peptide (and homologs) cleaves at very high efficiency immediately after translation of the ORF, enabling the expression of multiple peptides from a single ORF. A problem with the use of the 2A peptide to cleave between different peptides in the same ORF is that expression is limited to a 1:1 ratio.

Thus there is a need for alternative methods for expressing more than one protein from a single vector which are not associated with the disadvantages described above.

SUMMARY OF ASPECTS OF THE INVENTION

The present invention is based on the determination that, when two signal-peptide containing proteins are co-expressed as a polyprotein which is cleaved after translation, it is possible to modify the relative "strength" of the signal peptides, and thus control the relative expression of the two proteins. This need not be limited to a pair of transgenes, but may be used to allow control of the relative expression of multiple proteins initially translated as a polyprotein.

As used herein, 'polyprotein' refers to a polypeptide sequence translated from a single nucleic acid construct as a single entity, but which comprises polypeptide sequences which are subsequently separated and which function as discrete entities (e.g. separate proteins).

Thus in a first aspect the present invention provides a nucleic acid construct comprising the following structure:

A-X-B in which
A is nucleic acid sequence encoding a first polypeptide which comprises a first signal peptide;
B is nucleic acid sequence encoding a second polypeptide which comprises a second signal peptide and
X is a nucleic acid sequence which encodes a cleavage site, wherein the first signal peptide or the second signal peptide comprises one or more mutation(s) such that it has fewer hydrophobic amino acids.

The mutated signal peptide may have fewer hydrophobic amino acids than the "wild-type" signal peptide sequence from which it is derived.

The mutated signal peptide may have fewer hydrophobic amino acids than the signal peptide of the other polypeptide.

The hydrophobic amino acid(s) may be selected from the group: Alanine (A); Valine (V); Isoleucine (I); Leucine (L); Methionine (M); Phenylalanine (F); Tyrosine (Y); Tryptophan (W).

The first signal peptide and the second signal peptide may be derivable from the same sequence, but one signal peptide may comprise one or more amino acid deletions or substitutions to remove or replace one or more hydrophobic amino acids compared to the other signal peptide.

As explained in more detail below, signal sequences have a tripartite structure, consisting of a hydrophobic core region (h-region) flanked by an n- and c-region. The first signal peptide and the second signal peptide may have identical n- and c-regions, but may differ in the h-region: the h-region of one signal peptide having more hydrophobic amino acids that the other signal peptide.

The hydrophobic amino acid(s) deleted or replaced from the signal peptide may be selected from the group: Alanine (A); Valine (V); Isoleucine (I); Leucine (L); Methionine (M); Phenylalanine (F); Tyrosine (Y); Tryptophan (W).

The hydrophobic amino acid(s) deleted or replaced from the signal peptide may be selected from the group: Valine (V); Isoleucine (I); Leucine (L); and Tryptophan (W).

The signal peptide of one polypeptide may comprise up to five more hydrophobic amino acids than the other signal peptide. The altered signal peptide may have up to 10%, up to 20%, up to 30%, up to 40% or up to 50% of its hydrophobic amino acids replaced or removed.

The first and second polypeptides may be and signal peptide-containing polypeptides, such as secreted, transmembrane or organelle proteins. The present invention enables the relative expression of the proteins to be controlled i.e. the relative amounts of the proteins in the relevant compartment. For secreted proteins, the present invention enables the relative amounts of the proteins produced by a cell to be controlled. For transmembrane proteins, the present invention enables the relative cell surface expression of the two (or more) proteins to be controlled. For organelle proteins, the present invention enables the relative expression of the proteins to be controlled within, or on the membrane of, the organelle in question.

The first and second polypeptides may both be transmembrane proteins, such as T cell receptors or chimeric antigen receptors (CARs).

Where the first and second proteins are transmembrane proteins, the difference between the first and the second signal peptides may be such that, when the nucleic acid construct is expressed in a cell, there is differential relative expression of the first and second polypeptides at the cell surface.

X may be a nucleic acid sequence encoding a self-cleaving peptide, a furin cleavage site or a Tobacco Etch Virus cleavage site.

X may, for example, encode a 2A self-cleaving peptide from an aphtho- or a cardiovirus or a 2A-like peptide.

In a second aspect, the present invention provides a vector comprising a nucleic acid construct according to any preceding claim.

The vector may, for example, be a retroviral vector or a lentiviral vector.

In a third aspect, there is provided a cell comprising a nucleic acid construct according to the first aspect of the invention or a vector according to the second aspect of the invention.

In this third aspect, there is also provided a cell which comprises two chimeric antigen receptors having different signal peptides.

The two signal peptides may have a different number of hydrophobic amino acids.

In this aspect, the chimeric antigen receptor having a signal peptide with the greater number of hydrophobic amino acids may be more highly expressed at the cell surface than the chimeric antigen receptor having a signal peptide with the smaller number of hydrophobic amino acids.

There is also provided a cell which comprises two chimeric antigen receptors having different signal peptides, wherein the signal peptide of one chimeric antigen comprises one or more mutations such that it has fewer hydrophobic amino acids.

The chimeric antigen receptor having a mutated signal peptide may be expressed at a lower level at the cell surface than the chimeric antigen receptor having an unmutated signal peptide.

The cell may be a cytolytic immune cell, such as a T cell or a natural killer (NK) cell.

In a fourth aspect, there is provided a method for making a cell according to the fourth aspect of the invention which comprises the step of introducing a nucleic acid construct according to the first aspect of the invention or a vector according to the second aspect of the invention into a cell.

In a fifth aspect, there is provided a method for modulating the relative cell surface expression of a first signal peptide-containing protein expressed from a single nucleic acid construct with a second signal peptide-containing protein which comprises the step of mutating the nucleic acid sequence which encodes the signal peptide of one protein in order to remove or replace one or more hydrophobic amino acids in comparison with the signal peptide of the other protein.

The removal or replacement of hydrophobic amino acids from the signal peptide of a transmembrane protein reduces the amount of the transmembrane protein expressed on the cell surface, compared to a transmembrane protein having an unmodified signal peptide. As such, the relative expression level of a transmembrane protein derived from a polyprotein including a second polypeptide can be modulated. Where the transmembrane protein is only active at the cell surface (or predominantly active at the cell surface), reducing the relative cell surface expression of the protein also reduces its relative activity.

This invention can be extended to modulate the relative expression of three or more proteins expressed as a concatenated polypeptide, separated by cleavage sites and relative surface expression dictated by signal peptides of differing activity.

DETAILED DESCRIPTION

The present invention provides a nucleic acid construct comprising the following structure:

A-X-B in which

A is nucleic acid sequence encoding a first polypeptide which comprises a first signal peptide;

B is nucleic acid sequence encoding a second polypeptide which comprises a second signal peptide and X is a nucleic acid sequence which encodes a cleavage site, wherein the first signal peptide or the second signal peptide comprises one or more mutation(s) such that it has fewer hydrophobic amino acids.

Nucleic Acid Construct

Polypeptide

The polypeptides made by the nucleic acid construct of the invention are signal peptide-containing polypeptides, such as secreted, transmembrane or organelle proteins.

Signal Peptide

Figure 1:
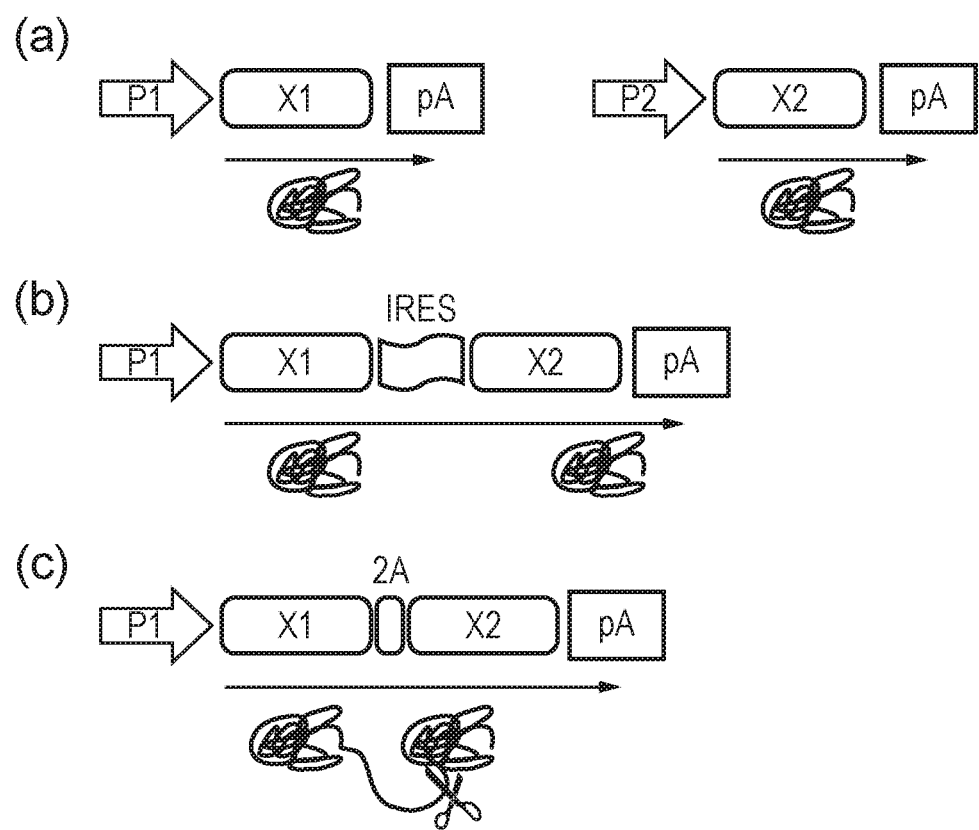
FIG. 1: Methods utilised to express different proteins from the same vector
(a) Two different promoters within the same cassette result in two different transcripts which each give rise to separate proteins. (b) Use of an Internal Ribosome Entry sequence (IRES) leads to a single transcript which is translated into two separate proteins. (c) Use of the FMDV 2A peptide results in a single transcript, and a single polyprotein which rapidly cleaves into two separate proteins.
Figure 2:
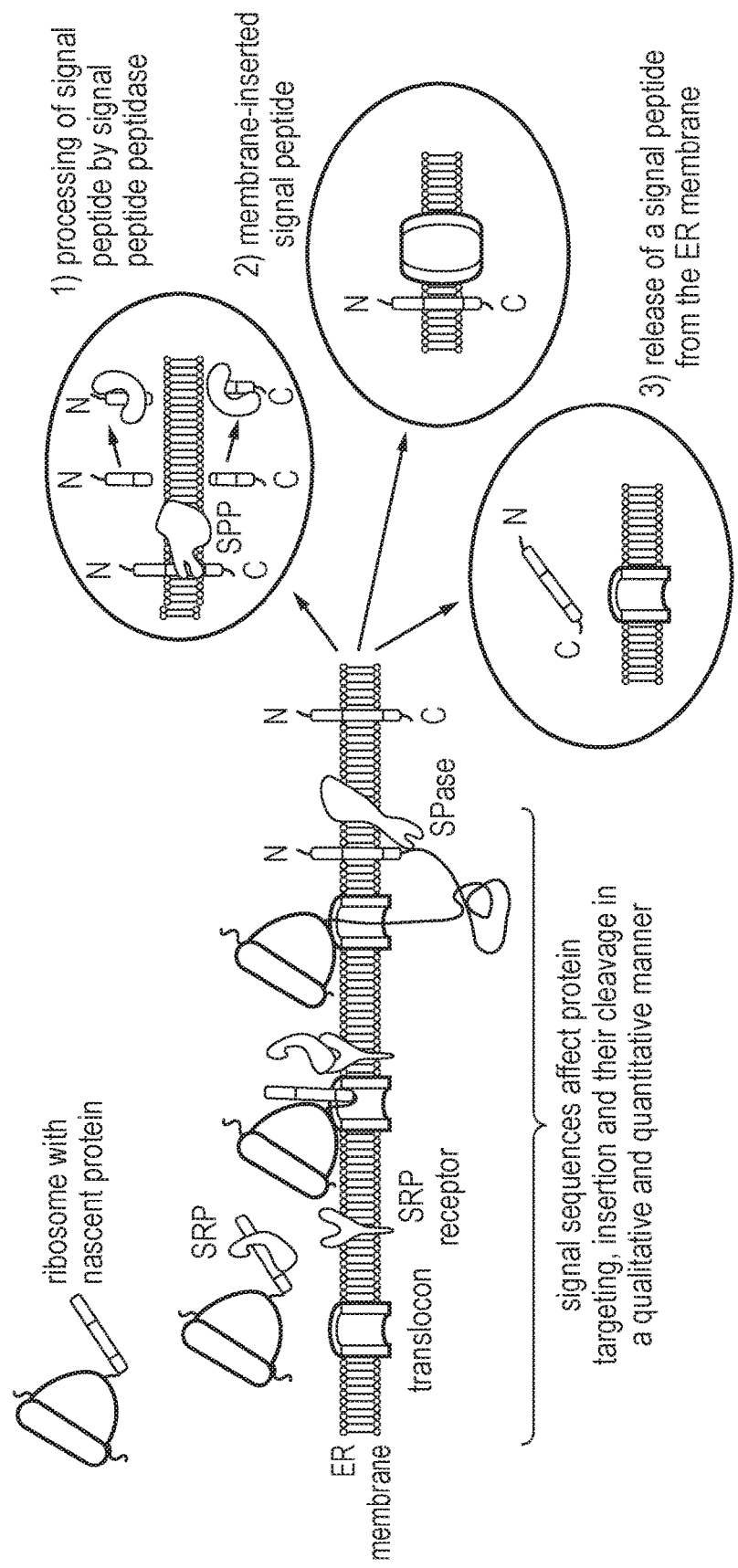
FIG. 2: Schematic diagram illustrating the function of signal sequences in protein targeting
Figure 3:
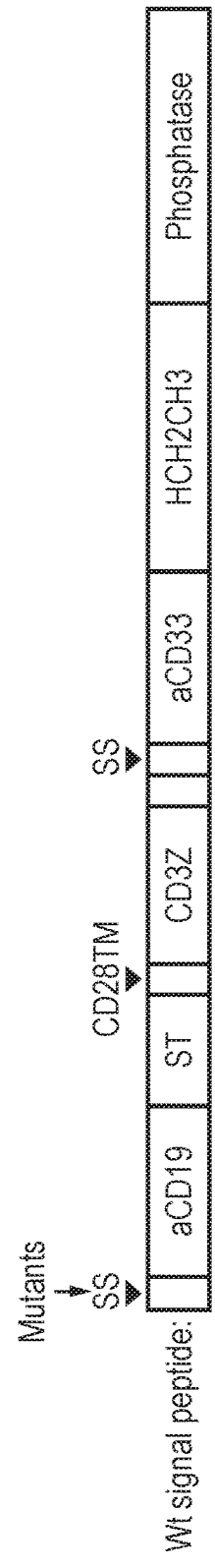
FIG. 3: Schematic diagram of nucleic acid construct encoding two CARs

The polypeptides A and B (and optionally others, C, D etc) encoded by the nucleic acid construct of the invention each comprise may a signal sequence so that when the polypeptide is expressed inside a cell the nascent protein is directed to the endoplasmic reticulum (ER) (see FIG. 2a).

The term "signal peptide" is synonymous with "signal sequence".

A signal peptide is a short peptide, commonly 5-30 amino acids long, present at the N-terminus of the majority of newly synthesized proteins that are destined towards the secretory pathway. These proteins include those that reside either inside certain organelles (for example, the endoplasmic reticulum, golgi or endosomes), are secreted from the cell, and transmembrane proteins.

Signal peptides commonly contain a core sequence which is a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide is commonly positioned at the amino terminus of the molecule, although some carboxy-terminal signal peptides are known.

As mentioned above, signal sequences have a tripartite structure, consisting of a hydrophobic core region (h-region) flanked by an n- and c-region. The latter contains the signal peptidase (SPase) consensus cleavage site. Usually, signal sequences are cleaved off co-translationally, the resulting cleaved signal sequences are termed signal peptides.

In the signal peptide from the murine Ig kappa chain V-III region, which has the sequence: METDTLILWVLLLL-VPGSTG (SEQ ID NO: 35): the n-region has the sequence METD; the h-region (shown in bold) has the sequence TLILWVLLLV; and the c-region has the sequence PGSTG.

In the nucleic acid construct of the present invention the signal sequence of the two (or more) polypeptides differ in their h-regions. One polypeptide (which has higher relative expression) has a greater number of hydrophobic amino acids in the h-region that the other polypeptide (which has lower relative expression). The signal peptide of the polypeptide with lower relative expression may comprise one or more amino acid mutations, such as substitutions or deletions, of hydrophobic amino acids in the h-region than the signal peptide of the polypeptide with lower relative expression.

The first signal peptide and the second signal peptide may have substantially the same n- and c-regions, but differ in the h-region as explained above. "Substantially the same" indicates that the n- and c-regions may be identical between the first and second signal peptide or may differ by one, two or three amino acids in the n- or c-chain, without affecting the function of the signal peptide.

The hydrophobic amino acids in the core may, for example, be: Alanine (A); Valine (V); Isoleucine (I); Leucine (L); Methionine (M); Phenylalanine (F); Tyrosine (Y); or Tryptophan (W).

The hydrophobic acids mutated in order to alter signal peptide efficiency may be any from the above list, in particular: Valine (V); Isoleucine (I); Leucine (L); and Tryptophan (W).

Of the residues in the h-region, one signal peptide (for example, the altered signal peptide) may comprise at least 10%, 20%, 30%, 40% or 50% fewer hydrophobic amino acids than the other signal peptide (for example, the unaltered signal peptide).

Where the h-region comprises 5-15 amino acids, one signal peptide may comprise 1, 2, 3, 4 or 5 more hydrophobic amino acids than the other signal peptide.

The altered signal peptide may comprise 1, 2, 3, 4 or 5 amino acid deletions or substitutions of hydrophobic amino acids. Hydrophobic amino acids may be replaced with non-hydrophobic amino acids, such as hydrophilic or neutral amino acids.

Signal sequences can be detected or predicted using software techniques (see for example, http COLON-SLASH-SLASH www.predisi.de/).

A very large number of signal sequences are known, and are available in databases. For example, http COLON-SLASH-SLASH www.signalpeptide.de lists 2109 confirmed mammalian signal peptides in its database.

Table 1 provides a list of signal sequences purely for illustrative purposes. The hydrophobic core is highlighted in bold. This includes examples of amino acids which may be substituted or removed for the purposes of the present invention.

TABLE 1

| Accession Number | Entry Name | Protein Name | Length | Signal Sequence (hydrophobic core) | SEQ ID NO: |
|---|---|---|---|---|---|
| P01730 | CD4_HUMAN | T-cell surface glycoprotein CD4 | 25 | MNRGVPFRHLLLVLQLALLPAATQG | 36 |
| P08575 | CD45_HUMAN | Leukocyte common antigen | 23 | MYLWLKLLAFGFAFLDTEVFVTG | 37 |
| P01732 | CD8A_HUMAN | T-cell surface glycoprotein CD8 alpha chain | 21 | MALPVTALLLPLALLLHAARP | 38 |
| P10966 | CD8B_HUMAN | T-cell surface glycoprotein CD8 beta chain | 21 | MRPRLWLLLAAQLTVLHGNSV | 39 |
| P06729 | CD2_HUMAN | T-cell surface antigen CD2 | 24 | MSFPCKFVASFLLIFNVSSKGAVS | 40 |
| P06127 | CD5_HUMAN | T-cell surface glycoprotein CD5 | 24 | MPMGSLQPLATLYLLGMLVASCLG | 41 |

TABLE 1-continued

| Accession Number | Entry Name | Protein Name | Length | Signal Sequence (hydrophobic core) | SEQ ID NO: |
|---|---|---|---|---|---|
| P09564 | CD7_HUMAN | T-cell antigen CD7 | 25 | MAGPPRLLLLPLLLALARGLPGALA | 42 |
| P17643 | TYRP1_HUMAN | 5,6-dihydroxyindole-2-carboxylic acid oxidase | 24 | MSAPKLLSLGCIFFPLLLFQQARA | 43 |
| P00709 | LALBA_HUMAN | Alpha-lactalbumin | 19 | MRFFVPLFLVGILFPAILA | 44 |
| P16278 | BGAL_HUMAN | Beta-galactosidase | 23 | MPGFLVRILPLLLVLLLLGPTRG | 45 |
| P31358 | CD52_HUMAN | CAMPATH-1 antigen | 24 | MKRFLFLLLTISLLVMVQIQTGLS | 46 |
| Q6YHK3 | CD109_HUMAN | CD109 antigen | 21 | MQGPPLLTAAHLLCVCTAALA | 47 |
| P01024 | CO3_HUMAN | Complement C3 | 22 | MGPTSGPSLLLLLLTHLPLALG | 48 |
| P10144 | GRAB_HUMAN | Granzyme B | 18 | MQPILLLLAFLLLPRADA | 49 |
| P04434 | KV310_HUMAN | Ig kappa chain V-III region VH | 20 | MEAPAQLLFLLLLWLPDTTR | 50 |
| P06312 | KV401_HUMAN | Ig kappa chain V-IV region | 20 | MVLQTQVFISLLLWISGAYG | 51 |
| P06319 | LV605_HUMAN | Ig lambda chain V-VI region EB4 | 19 | MAWAPLLLTLLAHCTDCWA | 52 |
| P31785 | IL2RG_HUMAN | Cytokine receptor common gamma chain | 22 | MLKPSLPFTSLLFLQLPLLGVG | 53 |
| Q8N4F0 | BPIL1_HUMAN | Bactericidal/permeability-increasing protein-like 1 | 20 | MAWASRLGLLLALLLPVVGA | 54 |
| P55899 | FCGRN_HUMAN | IgG receptor FcRn large subunit p51 | 23 | MGVPRPQPWALGLLLFLLPGSLG | 55 |

The mutated signal peptide comprises one or more mutation(s) such that it has fewer hydrophobic amino acids than the wild-type signal peptide from which it is derived. The term "wild type" means the sequence of the signal peptide which occurs in the natural protein from which it is derived. For example, the signal peptide described in the examples is the signal peptide from the murine Ig kappa chain V-III region, which has the wild-type sequence: METDTLILWV LLLLVPGSTG (SEQ ID NO: 35).

The term "wild-type" also includes signal peptides derived from a naturally occurring protein which comprise one or more amino acid mutations in the n- or c-region. For example it is common to modify a natural signal peptide with a conserved amino acid substitution on the N-terminus to introduce a restriction site. Such modified signal peptide sequences (which do not comprise any mutations in the h-region) are considered "wild-type" for the purposes of the present invention.

The present invention also relates to synthetic signal peptide sequences, which cannot be defined with reference to a wild-type sequence. In this embodiment, the signal peptide of the one polypeptide comprises fewer hydrophobic amino acids than the signal sequence of the other polypeptide. The two signal sequences may be derived from the same synthetic signal peptide sequence, but differ in the number of hydrophobic amino acids in the core region.

Transmembrane Protein

The present invention enables modulation of the relative expression of a transmembrane surface protein. The transmembrane surface protein is a protein which is expressed at the cell surface. When expressed at the cell surface at least one domain of the transmembrane protein is exoplasmic (i.e. on the exterior of the cell).

The transmembrane protein may be a single-pass transmembrane protein, i.e. it may comprise a single transmembrane domain or it may comprise multiple transmembrane domains.

Transmembrane proteins may be classified by topology i.e. with reference to the position of the N- and C-terminal domains. Types I, II, and III transmembrane proteins are single-pass molecules, while type IV trans-membrane proteins are multiple-pass molecules. Type I transmembrane proteins are anchored to the lipid membrane with a stop-transfer anchor sequence and have their N-terminal domains targeted to the ER lumen during synthesis (and the extracellular space, when the mature form is located on the plasma membrane). Type II and III are anchored with a signal-anchor sequence, with type II being targeted to the ER lumen with its C-terminal domain, while type III have their N-terminal domains targeted to the ER lumen. Type IV is subdivided into IV-A, with their N-terminal domains targeted to the cytosol and IV-B, with an N-terminal domain targeted to the lumen.

The transmembrane protein(s) made by the nucleic acid construct of the present invention may be any of the types I-IV.

The transmembrane domain may be any protein structure which is thermodynamically stable in a membrane. This is typically an alpha helix comprising of several hydrophobic residues. The transmembrane domain of any transmembrane protein can be used to supply the transmembrane portion. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e., a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good stability.

The structure and processing of Type I transmembrane proteins is well known in the art. Such proteins typically comprise an extracellular domain, a transmembrane domain and an intracellular endodomain, and are single-pass molecules with a single a-helix passing through the cell membrane.

Type I transmembrane proteins typically have a signal peptide which is quickly recognized by the endoplasmic reticulum (ER) and the protein in translation is therefore quickly re-directed into the ER. A hydrophobic helix locks then anchors the protein in the membrane of the ER.

As mentioned above, Type I transmembrane proteins are anchored to the lipid membrane with a stop-transfer anchor sequence. The stop-transfer sequence halts the further translocation of the polypeptide and acts as a transmembrane anchor.

As used herein, the term Type I transmembrane protein encompasses any protein which comprises a Type I transmembrane domain and a stop-transfer anchor sequence and is, in the absence of an exogenous intracellular retention signal, targeted for expression on the cell surface.

Various type 1 transmembrane proteins which are suitable for use in the present invention are known in the art. Such proteins include, but are not limited to inhibitory receptors, stimulatory receptors, cytokine receptors and G-Proteins.

The transmembrane protein(s) may be a T-cell receptor α or β chain.

The transmembrane protein(s) may be a Chimeric Antigen Receptor (CAR).

CARs are proteins which graft an antigen binding domain to the effector function of a T-cell. Their usual form is that of a type I transmembrane domain protein with an antigen recognizing amino terminus, a spacer, a transmembrane domain all connected to a compound endodomain which transmits T-cell survival and activation signals.

The antigen binding domain may be derived from an antibody or antibody mimetic, or it may be another entity which specifically binds the antigen, such as a ligand.

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

It is also possible for the signalling endodomain to be present on a separate molecule. The term "CAR" in connection with the present invention also encompasses a molecule which comprises an antigen binding domain connected to a transmembrane domain. Such a CAR may be capable of interacting with a separate intracellular signalling domain in order to stimulate T-cell activation.

In the present invention, either of the nucleic acid sequences A or B may be a nucleic acid sequence which encodes a transmembrane protein comprising a signal peptide.

Most transmembrane proteins of interest are only active, or are predominantly active when at the cell membrane. Therefore the use of an inefficient signal peptide reduces the relative expression of the protein at the cell surface and therefore reduces the relative activity of the protein.

Polyprotein

The nucleic acid construct of the present invention may encode a polyprotein, which comprises the first and second polypeptides.

The first and second polypeptides may be chimeric antigen receptors (CARs).

The nucleic acid construct described in the Examples encodes the following polyprotein which comprises the various components in the order they are listed:

Signal peptide derived from Mouse Ig kappa chain V-III region:
METDTLILWVLLLLVPGSTG (SEQ ID NO: 35) (see below)

scFv aCD19:
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITKAGGGGSGGGGSGGGGSGGGGSEVKLQESGPGLVAPSQSL

SVTCTVSGVSLPDYGVSWIRQPPRKGLEWLGVIWGSETTYYNSALKSRL

TIIKDNSKSQVFLKMNSLQTDDTAIYYCAKHYYYGGSYAMDYWGQGTSV

TVS (SEQ ID NO: 56)

Linker:
SD

Human CD8aSTK:
PTTTPAPRPPTPAPTIASQPLSLRPEACRPAAGGAVHTRGLDFACDI (SEQ ID NO: 57)

Human CD28TM:
FWVLVVVGGVLACYSLLVTVAFIIFWV (SEQ ID NO: 58)

Human CD3zeta intracellular domain:
RRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTAT
KDTYDALHMQALPPR (SEQ ID NO: 59)

2A peptide:
RAEGRGSLLTCGDVEENPGP (SEQ ID NO: 60)

Signal peptide derived from mouse Ig kappa:
MAVPTQVLGLLLLWLTDA (SEQ ID NO: 61)

scFv aCD33:
RCDIQMTQSPSSLSASVGDRVTITCRASEDIYFNLVWYQQKPGKAPKWY
DTNRLADGVPSRFSGSGSGTQYTLTISSLQPEDFATYYCQHYKNYPLTF
GQGTKLEIKRSGGGGSGGGGSGGGGSGGGGSRSEVQLVESGGGLVQPGG
SLRLSCAASGFTLSNYGMHWIRQAPGKGLEWVSSISLNGGSTYYRDSVK
GRFTISRDNAKSTLYLQMNSLRAEDTAVYYCAAQDAYTGGYFDYWGQGT
LVTVSSM (SEQ ID NO: 62)

Linker:
DPA

Hinge and Fc derived from human IgG1 with mutations to prevent FcRg association (HCH2CH3pvaa):
EPKSPDKTHTCPPCPAPPVAGPSVFLFPPKPKDTLMIARTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO: 63)

Linker:
KDPK (SEQ ID NO: 64)

Human CD148TM:
AVFGCIFGALVIVTVGGFIFW (SEQ ID NO: 65)

Human CD148 intracellular domain:
RKKRKDAKNNEVSFSQIKPKKSKLIRVENFEAYFKKQQADSNCGFAEEY
EDLKLVGISQPKYAAELAENRGKNRYNNVLPYDISRVKLSVQTHSTDDY
INANYMPGYHSKKDFIATQGPLPNTLKDFWRMVWEKNVYAIIMLTKCVE
QGRTKCEEYWPSKQAQDYGDITVAMTSEIVLPEWTIRDFTVKNIQTSES
HPLRQFHFTSWPDHGVPDTTDLLINFRYLVRDYMKQSPPESPILVHCSA
GVGRTGTFIAIDRLIYQIENENTVDVYGIVYDLRMHRPLMVQTEDQYVF
LNQCVLDIVRSQKDSKVDLIYQNTTAMTIYENLAPVTTFGKTNGYIA (SEQ ID NO: 66)

The signal sequence of from murine Ig kappa chain V-III region, which has the sequence: METDTLILWVLLLL-VPGSTG (SEQ ID NO: 35) (hydrophobic residues highlighted in bold) is altered as described in the Examples. Hydrophobic residues were sequentially deleted from the hydrophobic core in order to reduce the level of expression of the anti-CD19 CAR.

Cleavage Site

The nucleic acid construct of the first aspect of the invention comprises a sequence encoding a cleavage site positioned between nucleic acid sequences which encode first and second polypeptides, such that first and second polypeptides can be expressed as separate entities.

The cleavage site may be any sequence which enables the polypeptide comprising the first and second polypeptides to become separated.

The term "cleavage" is used herein for convenience, but the cleavage site may cause the first and second polypeptidess to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode first and second polypeptides, causes the first and second polypeptides to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg (SEQ ID NO: 67 and SEQ ID NO: 68)) and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (SEQ ID NO: 69) (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the first and second polypeptides and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus.

The C-terminal 19 amino acids of the longer cardiovirus protein, together with the N-terminal proline of 2B mediate "cleavage" with an efficiency approximately equal to the apthovirus FMDV 2a sequence. Cardioviruses include encephalomyocarditis virus (EMCV) and Theiler's murine encephalitis virus (TMEV).

Mutational analysis of EMCV and FMDV 2A has revealed that the motif DxExNPGP is intimately involved in "cleavage" activity (Donnelly et al (2001) as above).

The cleavage site of the present invention may comprise the amino acid sequence: $Dx_1Ex_2NPGP$, where $x_1$ and $x_2$ are any amino acid. $X_1$ may be selected from the following group: I, V, M and S. $X_2$ may be selected from the following group: T, M, S, L, E, Q and F.

For example, the cleavage site may comprise one of the amino acid sequences shown in Table 2.

TABLE 2

| Motif | | Present in: |
|---|---|---|
| DIETNPGP | (SEQ ID NO: 1) | Picornaviruses EMCB, EMCD, EMCPV21 |
| DVETNPGP | (SEQ ID NO: 2) | Picornaviruses MENGO and TMEBEAN; Insect virus DCV, ABPV |
| DVEMNPGP | (SEQ ID NO: 3) | Picornaviruses TMEGD7 and TMEBEAN |
| DVESNPGP | (SEQ ID NO: 4) | Picornaviruses FMDA10, FMDA12, FMDC1, FMD01K, FMDSAT3, FMDVSAT2, ERAV; Insect virus CrPV |
| DMESNPGP | (SEQ ID NO: 5) | Picornavirus FMDV01G |
| DVELNPGP | (SEQ ID NO: 6) | Picornavirus ERBV; Porcine rotavirus |
| DVEENPGP | (SEQ ID NO: 7) | Picornavirus PTV-1; Insect virus TaV; Trypanosoma TSR1 |
| DIELNPGP | (SEQ ID NO: 8) | Bovine Rotavirus, human rotavirus |
| DIEQNPGP | (SEQ ID NO: 9) | Trypanosoma AP endonuclease |
| DSEFNPGP | (SEQ ID NO: 10) | Bacterial sequence T. maritima |

The cleavage site, based on a 2A sequence may be, for example 15-22 amino acids in length. The sequence may comprise the C-terminus of a 2A protein, followed by a proline residue (which corresponds to the N-terminal proline of 2B).

Mutational studies have also shown that, in addition to the naturally occurring 2A sequences, some variants are also active. The cleavage site may correspond to a variant sequence from a naturally occurring 2A polypeptide, have one, two or three amino acid substitutions, which retains the capacity to induce the "cleavage" of a polyprotein sequence into two or more separate proteins.

The cleavage sequence may be selected from the following which have all been shown to be active to a certain extent (Donnelly et al (2001) as above):

```
LLNFDLLKLAGDVESNPGP        (SEQ ID NO: 11)

LLNFDLLKLAGDVQSNPGP        (SEQ ID NO: 12)

LLNFDLLKLAGDVEINPGP        (SEQ ID NO: 13)

LLNFDLLKLAGDVEFNPGP        (SEQ ID NO: 14)

LLNFDLLKLAGDVESHPGP        (SEQ ID NO: 15)

LLNFDLLKLAGDVESEPGP        (SEQ ID NO: 16)

LLNFDLLKLAGDVESQPGP        (SEQ ID NO: 17)

LLNFDLLKLAGDVESNPGG        (SEQ ID NO: 18)
```

Based on the sequence of the DxExNPGP "a motif, "2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

```
YHADYYKQRLIHDVEMNPGP       (SEQ ID NO: 19)

HYAGYFADLLIHDIETNPGP       (SEQ ID NO: 20)

QCTNYALLKLAGDVESNPGP       (SEQ ID NO: 21)

ATNFSLLKQAGDVEENPGP        (SEQ ID NO: 22)

AARQMLLLLSGDVETNPGP        (SEQ ID NO: 23)

RAEGRGSLLTCGDVEENPGP       (SEQ ID NO: 24)

TRAEIEDELIRAGIESNPGP       (SEQ ID NO: 25)

TRAEIEDELIRADIESNPGP       (SEQ ID NO: 26)

AKFQIDKILISGDVELNPGP       (SEQ ID NO: 27)

SSIIRTKMLVSGDVEENPGP       (SEQ ID NO: 28)

CDAQRQKLLLSGDIEQNPGP       (SEQ ID NO: 29)

YPIDFGGFLVKADSEFNPGP       (SEQ ID NO: 30)
```

The cleavage site may comprise the 2A-like sequence shown as SEQ ID NO: 24 (RAEGRGSLLTCGDVEENPGP).

It has been shown that including an N-terminal "extension" of between 5 and 39 amino acids can increase activity (Donnelly et al (2001) as above). In particular, the cleavage sequence may comprise one of the following sequences or a variant thereof having, for example, up to 5 amino acid changes which retains cleavage site activity:

```
VTELLYRMKRAETYCPRPLAIHPTEARHKQKIVAPVKQTLNFDLLKLAG    (SEQ ID NO: 31)
DVESNPGP

LLAIHPTEARHKQKIVAPVKQTLNFDLLKLAGDVESNPGP            (SEQ ID NO: 32)

EARHKQKIVAPVKQTLNFDLLKLAGDVESNPGP                   (SEQ ID NO: 33)

APVKQTLNFDLLKLAGDVESNPGP                            (SEQ ID NO: 34)
```

Tunability

The relative expression of one or more protein(s) may be fine-tuned using the method of the invention by using signal peptides with different amounts or proportions of hydrophobic amino acids.

The tunability using different signal peptides is especially useful when one considers the expression of multiple proteins, each with their own relative expression. For example, consider a nucleic acid construct having the following structure:

A-X-B-Y-C in which

A, B and C are nucleic acid sequences encoding polypeptides; and

X and Y are nucleic acid sequences encodes cleavage sites.

The nucleic acid construct will encode three proteins A, B and C, any or all of which may be transmembrane proteins. If it is desired for A, B and C to be expressed such that the relative levels are A>B>C, then the nucleic acid sequence A may have a signal peptide with the most hydrophobic amino acids, the nucleic acid sequence B may have a signal peptide with a medium amount of hydrophobic amino acids, and the nucleic acid sequence C may have a signal peptide with the least hydrophobic amino acids.

Vector

The present invention also provides a vector comprising a nucleic acid construct according to the first aspect of the invention.

Such a vector may be used to introduce the nucleic acid construct into a host cell so that it expresses the first and second polypeptide.

The vector may, for example, be a plasmid or a viral vector, such as a retroviral vector or a lentiviral vector, or a transposon based vector or synthetic mRNA.

The vector may be capable of transfecting or transducing a mammalian cell, for example a T cell.

Cell

The present invention furthers provides a cell comprising a nucleic acid construct or vector of the present invention which expresses the first and second polypeptide encoded by the nucleic acid sequence.

The cell may be any eukaryotic cell capable of expressing a transmembrane protein at the cell surface, such as an immunological cell.

The cell may be a cytolytic immune cell, such as a T cell or natural killer cell.

Method

In a further aspect the present invention provides a method for making a cell according to the invention which comprises the step of introducing a nucleic acid construct or a vector of the invention into a cell.

The nucleic acid construct may be introduced by transduction or transfection.

The cell may be a cell isolated from a subject, for example a T cell or an NK cell isolated from a subject.

The present invention also provides a method for modulating the relative cell surface expression of a first protein expressed from a single nucleic acid construct with a second protein which comprises the step of mutating the nucleic acid sequence which encodes the signal peptide of one protein in order to remove or replace on or more hydrophobic amino acids in comparison with the signal peptide of the other protein.

The signal peptide may be altered by techniques known in the art, such as site directed mutagenesis and recombinant techniques.

The invention will now be further described by way of Examples, which are meant to serve to assist one of ordinary skill in the art in carrying out the invention and are not intended in any way to limit the scope of the invention.

EXAMPLES

Example 1—Using the Murine Ig Kappa Chain V-III Signal Sequence

Figure 4:
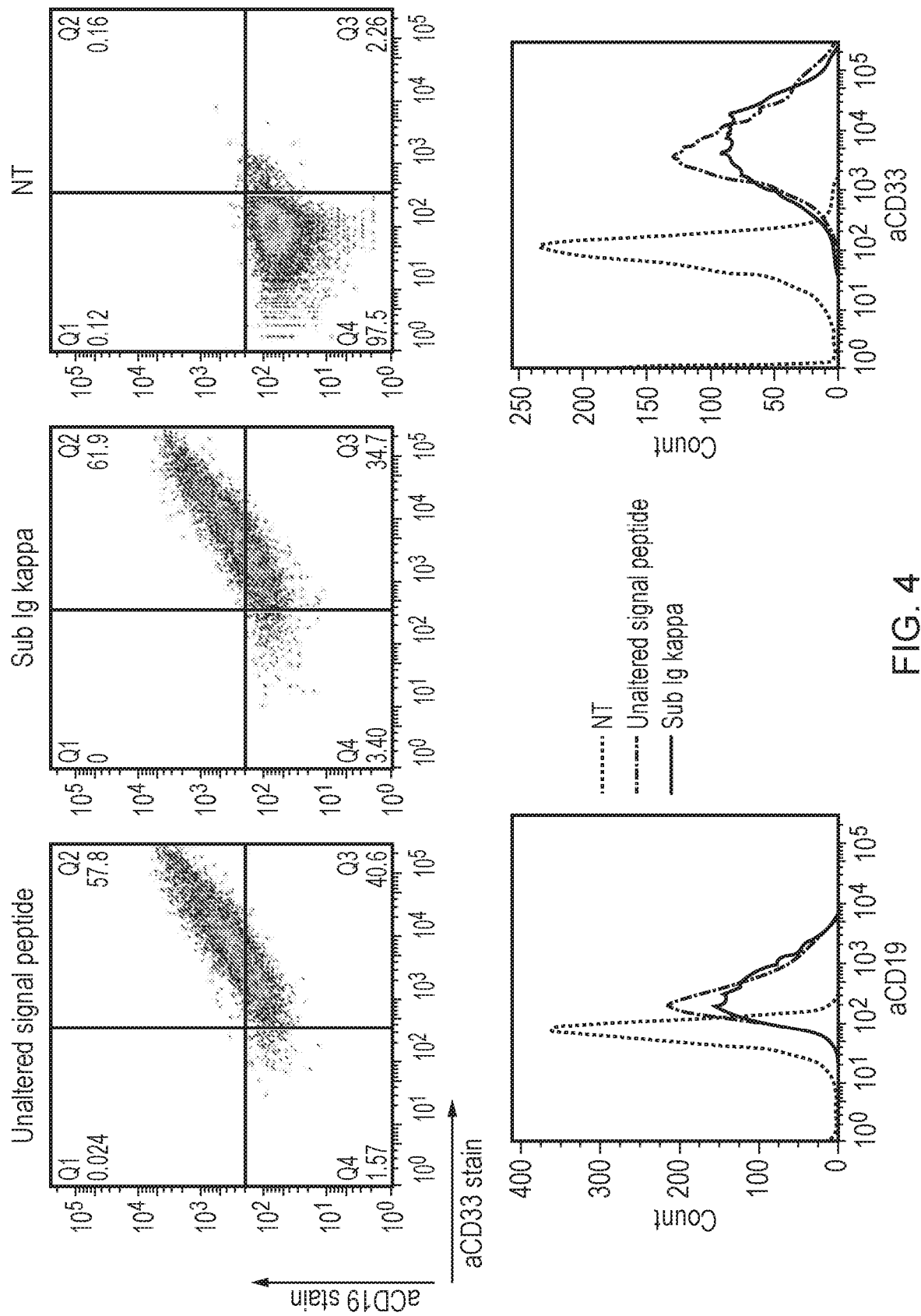
FIG. 4: Verifying the function of a substituted signal sequence.
PCT/GB2014/053452 describes vector system encoding two chimeric antigen receptors (CARs), one against CD19 and one against CD33. The signal peptide used for the CARs in that study was the signal peptide from the human CD8a signal sequence. For the purposes of this study, this was substituted with the signal peptide from the murine Ig kappa chain V-III region, which has the sequence: METDTLILWVLLLLVPGSTG (SEQ ID NO: 35) (hydrophobic residues highlighted in bold). In order to establish that the murine Ig kappa chain V-III signal sequence functioned as well as the signal sequence from human CD8a, a comparative study was performed. For both signal sequences, functional expression of the anti-CD33 CAR and the anti-CD19 CAR was observed.
Figure 5:
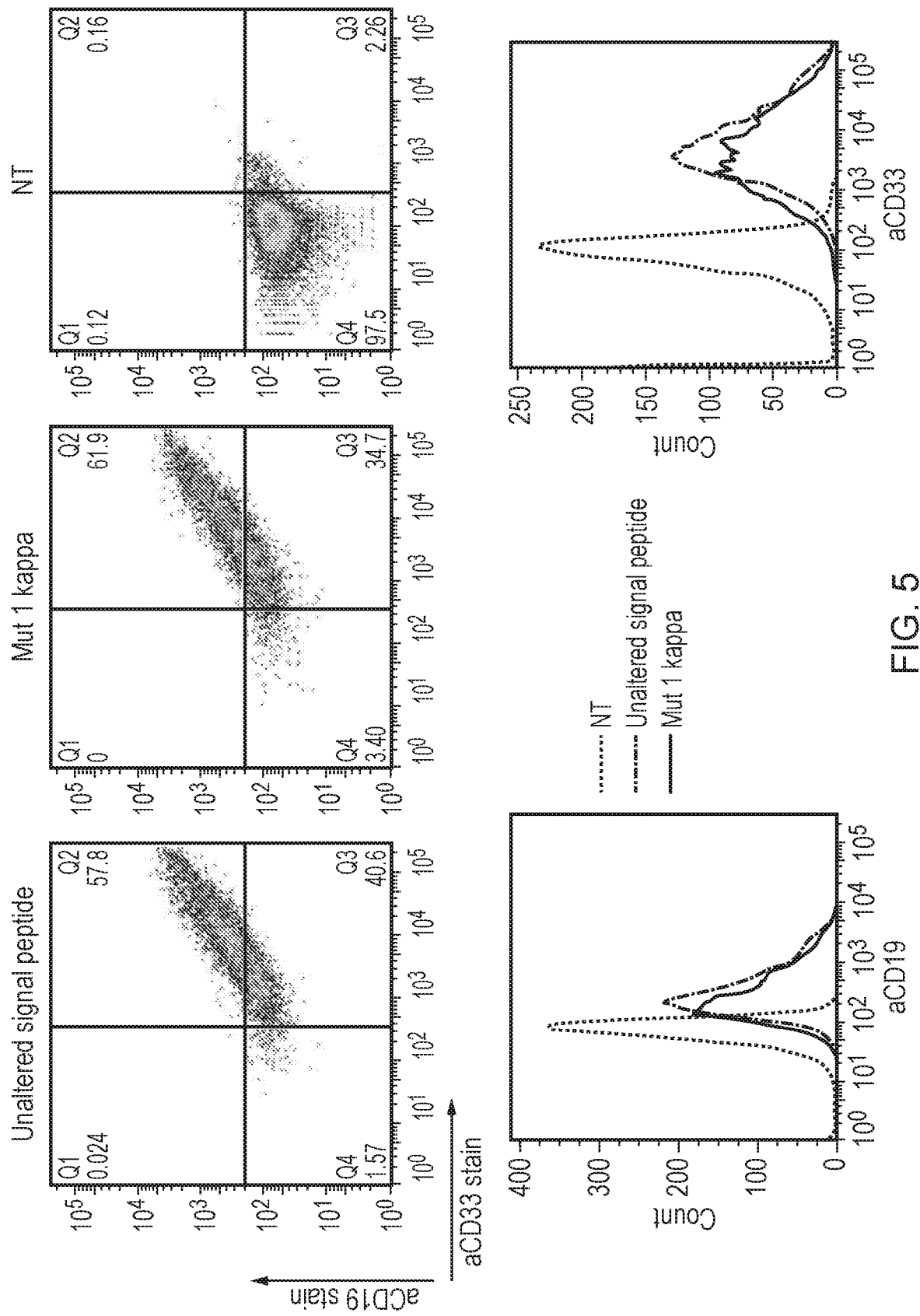
FIG. 5: Testing the effect of one amino acid deletion in the murine Ig kappa chain V-III. Mutant 1 kappa chain was created with the following deletion (shown in grey) in the h-region METDTLILWVLLLLVPGSTG (SEQ ID NO: 35) and the relative expression on the anti-CD33 CAR and the anti-CD19 CAR was observed.
Figure 6:
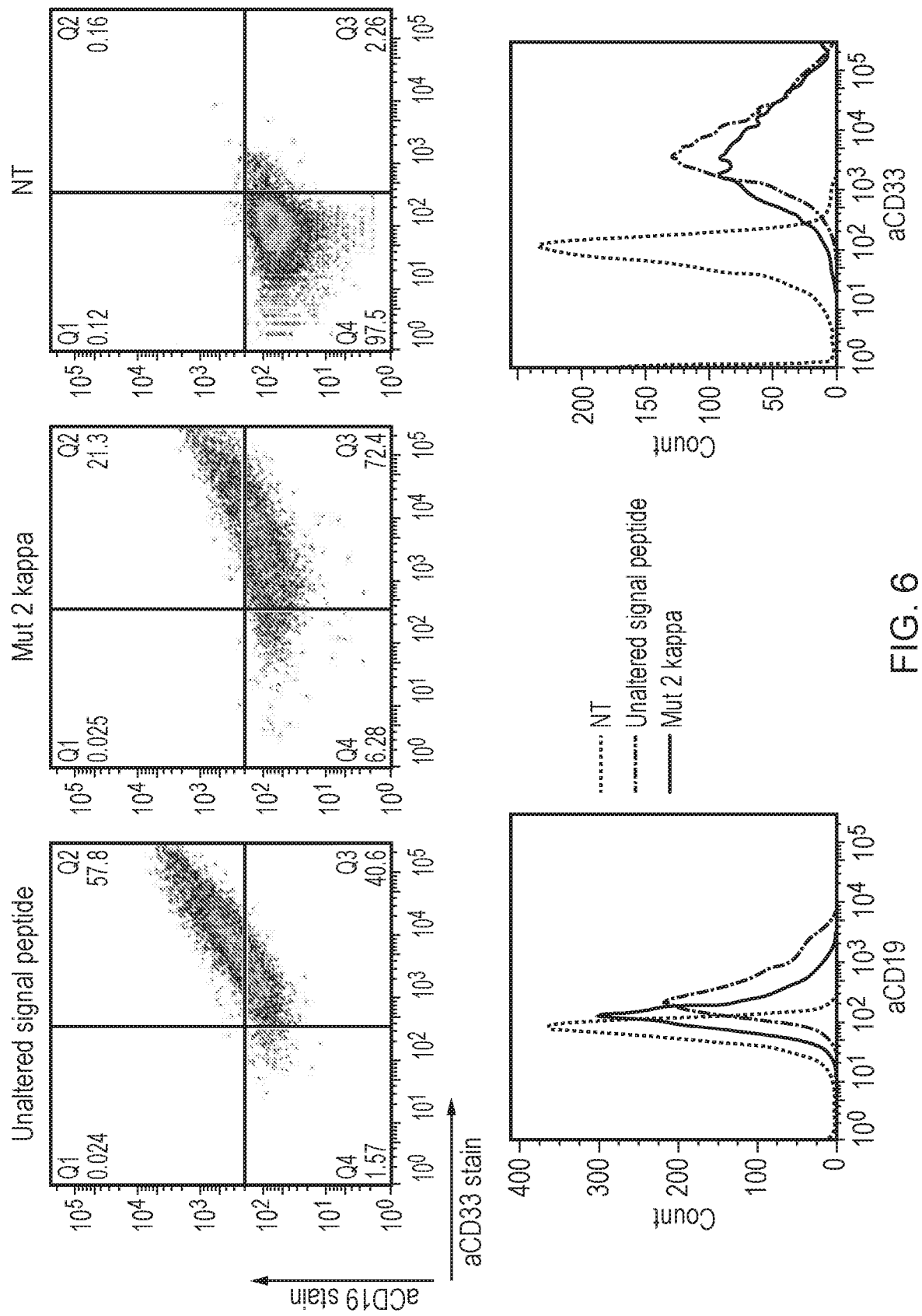
FIG. 6: Testing the effect of two amino acid deletions in the murine Ig kappa chain V-III. Mutant 2 kappa chain was created with the following deletions (shown in grey) in the h-region METDUILWVLLLIIVPGSTG (SEQ ID NO: 35) and the relative expression on the anti-CD33 CAR and the anti-CD19 CAR was observed.
Figure 7:
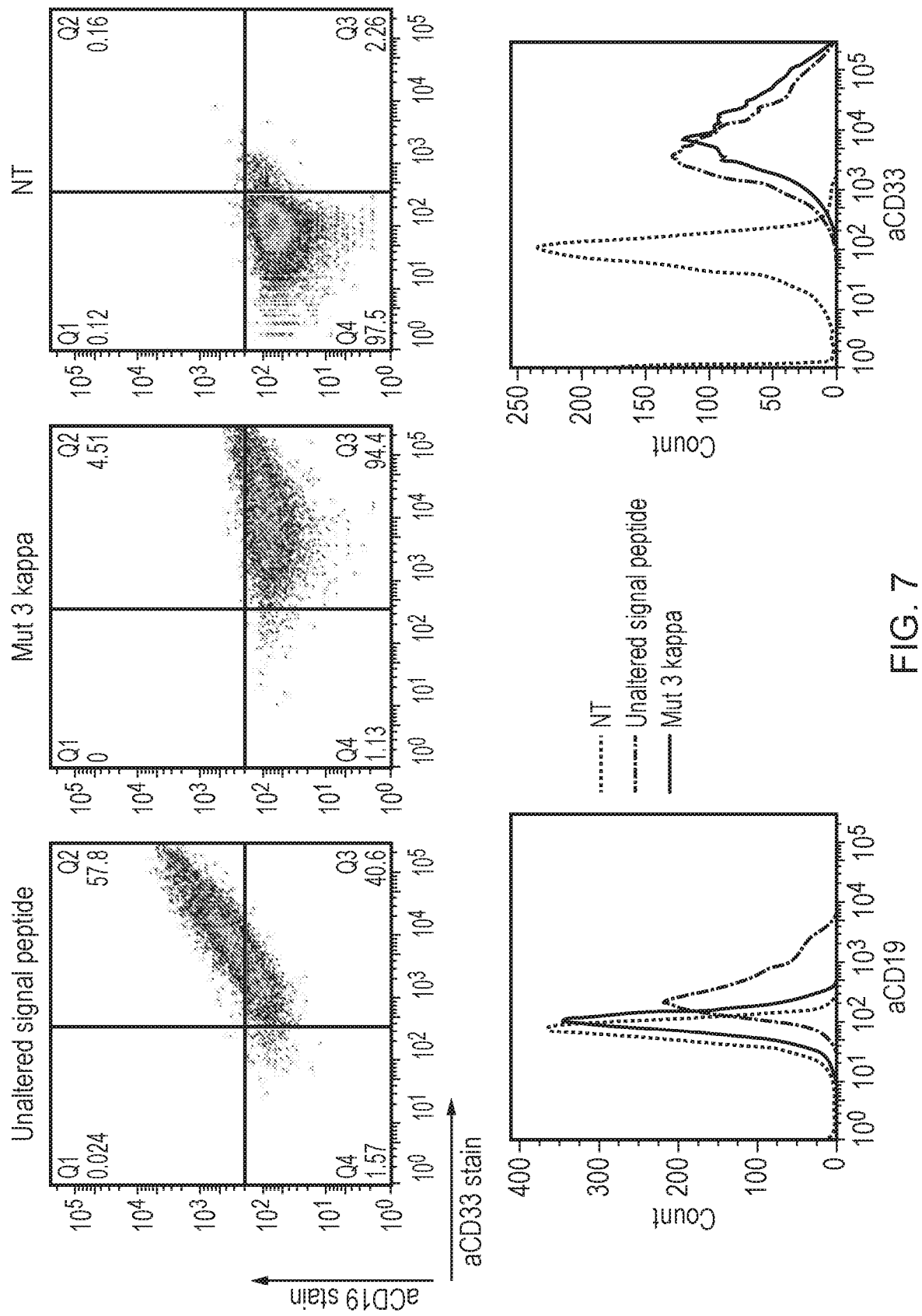
FIG. 7: Testing the effect of three amino acid deletions in the murine Ig kappa chain V-III. Mutant 2 kappa chain was created with the following deletions (shown in grey) in the h-region METDTLILWVLLLLVPGSTG (SEQ ID NO: 35) and the relative expression on the anti-CD33 CAR and the anti-CD19 CAR was observed.
Figure 8:
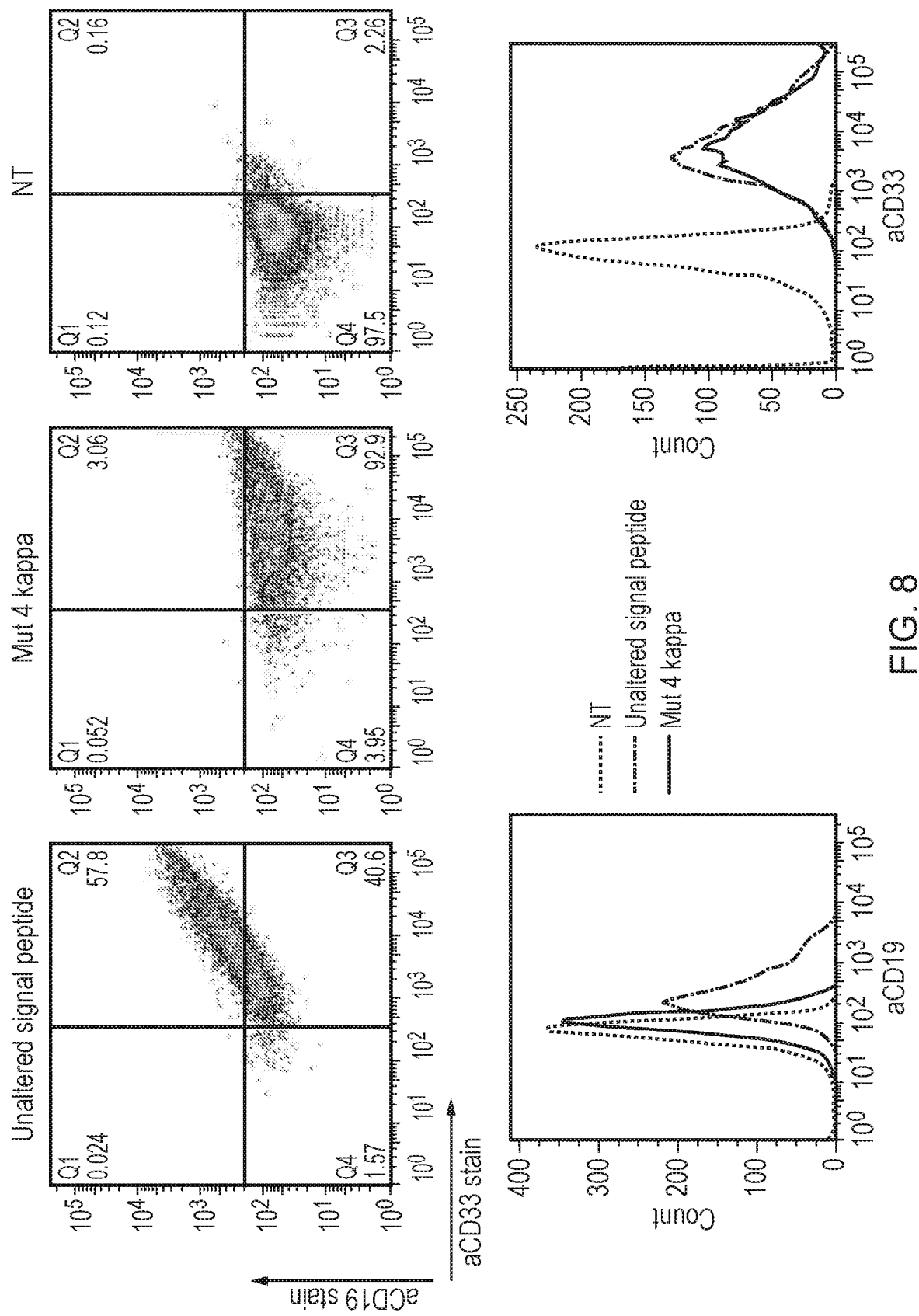
FIG. 8: Testing the effect of five amino acid deletions in the murine Ig kappa chain V-III. Mutant 2 kappa chain was created with the following deletions (shown in grey) in the h-region METDLILWVLLLLVPGSTG (SEQ ID NO: 35) and the relative expression on the anti-CD33 CAR and the anti-CD19 CAR was observed.

PCT/GB2014/053452 describes a vector system encoding two chimeric antigen receptors (CARs), one against CD19 and one against CD33. The signal peptide used for the CARs in that study was the signal peptide from the human CD8a signal sequence. For the purposes of this study, this was substituted with the signal peptide from the murine Ig kappa chain V-III region, which has the sequence: METDTLILWVLLLLVPGSTG (SEQ ID NO: 35) (hydrophobic residues highlighted in bold). In order to establish that the murine Ig kappa chain V-III signal sequence functioned as well as the signal sequence from human CD8a, a comparative study was performed. For both signal sequences, functional expression of the anti-CD33 CAR and the anti-CD19 CAR was observed. This substituted signal sequence and all subsequent mutations thereof were transiently transfected into 293T cells. Three days after transfection the 293T cells were stained with both soluble chimeric CD19 fused with rabbit Fc chain and soluble chimeric CD33 fused with mouse Fc chain. All cells were then stained with anti-Rabbit Fc-FITC and anti-mouse Fc-APC. Flow cytometry plots show the substituted signal sequence as a comparison with non-transfected (NT) and the construct with Cd8 signal sequences (FIG. 4). The murine Ig kappa chain V-III signal sequence was found to function as well as the signal sequence from human CD8a.

Example 2—Altering Relative Expression by Deleting Hydrophobic Residues in the Signal Peptide Hydrophobic residues were deleted in a stepwise fashion and the effect on the relative expression of the anti-CD33 CAR and the anti-CD19 CAR was observed. The effect of one, two, three and four amino acid deletions was investigated and the results are shown in FIGS. 5 to 8 respectively.

All mutant constructs showed a decrease in relative expression of the anti-CD19 CAR compared to the anti-CD33 CAR. The relative decrease of anti-CD19 CAR expression was greater with a greater number of amino acid deletions from 1 to 3, but then plateaued out (four deletions gave a similar decrease in expression as three deletions).

Modification of the signal sequences in a nucleic acid construct encoding two polypeptides can therefore be used to control the relative expression of the two polypeptides.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A nucleic acid construct comprising the following structure:

A-X-B in which
(a) A is nucleic acid sequence encoding a first polypeptide which comprises a first signal peptide attached to a first mature protein, the first signal peptide having a tripartite structure containing a hydrophobic core region (h-region) flanked by an n-region and a c-region,
(b) B is nucleic acid sequence encoding a second polypeptide which comprises a second signal peptide attached to a second mature protein, the second signal peptide having a tripartite structure containing a hydrophobic core region (h-region) flanked by an n-region and a c-region, and
(c) X is a nucleic acid sequence which encodes a cleavage site, wherein the first signal peptide and the second signal peptide are derived from the same signal sequence having the same n- and c-regions, but the first signal peptide or the second signal peptide differ in the h-region, one signal peptide having 1, 2, 3, 4, or 5 amino acid deletions or substitutions in the h-region to remove or replace one or more hydrophobic amino acids compared to the other signal peptide such that the signal peptide with the amino acid deletions or substitutions has 1, 2, 3, 4, or 5 fewer hydrophobic amino acids in the h-region than the other signal peptide, and wherein differences between the first and the second signal peptides in the h-region are such that when the nucleic acid construct is expressed in an eukaryotic cell, there is differential relative expression of the first and second mature proteins.

2. The nucleic acid construct according to claim 1, wherein the hydrophobic amino acid(s) is/are selected from the group consisting of Alanine (A), Valine (V), Isoleucine (I), Leucine (L), Methionine (M), Phenylalanine (F), Tyrosine (Y), and Tryptophan (W).

3. The nucleic acid construct according to claim 2, wherein the hydrophobic amino acid(s) is/are selected from the group consisting of Valine (V), Isoleucine (I), Leucine (L), and Tryptophan (W).

4. The nucleic acid construct according to claim 1, wherein the first and second polypeptides are both transmembrane proteins, and wherein there is differential relative expression of the first and second transmembrane proteins at the cell surface.

5. The nucleic acid construct according to claim 4, wherein the first and second transmembrane proteins are both chimeric antigen receptors (CARs).

6. The nucleic acid construct according to claim 1, wherein the cleavage site is a self-cleaving peptide, a furin cleavage site or a Tobacco Etch Virus cleavage site.

7. An expression vector comprising the nucleic acid construct according to claim 1.

8. A retroviral vector or a lentiviral vector according to claim 7.

9. An isolated eukaryotic cell comprising the nucleic acid construct according to claim 1.

10. The isolated eukaryotic cell according to claim 9 which is a T cell or a natural killer (NK) cell.

11. The isolated eukaryotic cell according to claim 9 that is an isolated mammalian cell.

* * * * *

SEQUENCE LISTING

```
<160> NUMBER OF SEQ ID NOS: 74

<210> SEQ ID NO 1
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 1

Asp Ile Glu Thr Asn Pro Gly Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 2
```

Asp Val Glu Thr Asn Pro Gly Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 3

Asp Val Glu Met Asn Pro Gly Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 4

Asp Val Glu Ser Asn Pro Gly Pro
1               5

<210> SEQ ID NO 5
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 5

Asp Met Glu Ser Asn Pro Gly Pro
1               5

<210> SEQ ID NO 6
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 6

Asp Val Glu Leu Asn Pro Gly Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 7

Asp Val Glu Glu Asn Pro Gly Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 8

```
Asp Ile Glu Leu Asn Pro Gly Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 9

Asp Ile Glu Gln Asn Pro Gly Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Cleavage site, self-cleaving peptide

<400> SEQUENCE: 10

Asp Ser Glu Phe Asn Pro Gly Pro
1               5

<210> SEQ ID NO 11
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 11

Leu Leu Asn Phe Asp Leu Leu Lys Leu Ala Gly Asp Val Glu Ser Asn
1               5                   10                  15

Pro Gly Pro

<210> SEQ ID NO 12
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 12

Leu Leu Asn Phe Asp Leu Leu Lys Leu Ala Gly Asp Val Gln Ser Asn
1               5                   10                  15

Pro Gly Pro

<210> SEQ ID NO 13
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 13

Leu Leu Asn Phe Asp Leu Leu Lys Leu Ala Gly Asp Val Glu Ile Asn
1               5                   10                  15

Pro Gly Pro

<210> SEQ ID NO 14
<211> LENGTH: 19
<212> TYPE: PRT
<213> ORGANISM: Artificial Sequence
```

```
<220> FEATURE:
<223> OTHER INFORMATION: Cleavage sequence, self-cleaving peptide

<400> SEQUENCE: 14

Leu Leu Asn Phe Asp Leu Leu Lys Leu Ala Gly Asp Val Glu Phe Asn
1               5                   10                  15

Pro Gly Pro

<210> SEQ ID NO 15
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 15

Leu Leu Asn Phe Asp Leu Leu Lys Leu Ala Gly Asp Val Glu Ser His
1               5                   10                  15

Pro Gly Pro

<210> SEQ ID NO 16
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 16

Leu Leu Asn Phe Asp Leu Leu Lys Leu Ala Gly Asp Val Glu Ser Glu
1               5                   10                  15

Pro Gly Pro

<210> SEQ ID NO 17
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 17

Leu Leu Asn Phe Asp Leu Leu Lys Leu Ala Gly Asp Val Glu Ser Gln
1               5                   10                  15

Pro Gly Pro

<210> SEQ ID NO 18
<211> LENGTH: 19
<212> TYPE: PRT
<213> ORGANISM: Artificial Sequence
<220> FEATURE:
<223> OTHER INFORMATION: Cleavage sequence, self-cleaving peptide

<400> SEQUENCE: 18

Leu Leu Asn Phe Asp Leu Leu Lys Leu Ala Gly Asp Val Glu Ser Asn
1               5                   10                  15

Pro Gly Gly

<210> SEQ ID NO 19
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 19
```

```
Tyr His Ala Asp Tyr Tyr Lys Gln Arg Leu Ile His Asp Val Glu Met
1               5                   10                  15

Asn Pro Gly Pro
            20
```

<210> SEQ ID NO 20
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 20

```
His Tyr Ala Gly Tyr Phe Ala Asp Leu Leu Ile His Asp Ile Glu Thr
1               5                   10                  15

Asn Pro Gly Pro
            20
```

<210> SEQ ID NO 21
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 21

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 22
<211> LENGTH: 19
<212> TYPE: PRT
<213> ORGANISM: Artificial Sequence
<220> FEATURE:
<223> OTHER INFORMATION: 2A-like self-cleaving peptide

<400> SEQUENCE: 22

```
Ala Thr Asn Phe Ser Leu Leu Lys Gln Ala Gly Asp Val Glu Glu Asn
1               5                   10                  15

Pro Gly Pro
```

<210> SEQ ID NO 23
<211> LENGTH: 19
<212> TYPE: PRT
<213> ORGANISM: Artificial Sequence
<220> FEATURE:
<223> OTHER INFORMATION: 2A-like self-cleaving peptide

<400> SEQUENCE: 23

```
Ala Ala Arg Gln Met Leu Leu Leu Leu Ser Gly Asp Val Glu Thr Asn
1               5                   10                  15

Pro Gly Pro
```

<210> SEQ ID NO 24
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 24

Arg Ala Glu Gly Arg Gly Ser Leu Leu Thr Cys Gly Asp Val Glu Glu
1               5                   10                  15

Asn Pro Gly Pro
            20

<210> SEQ ID NO 25
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 25

Thr Arg Ala Glu Ile Glu Asp Glu Leu Ile Arg Ala Gly Ile Glu Ser
1               5                   10                  15

Asn Pro Gly Pro
            20

<210> SEQ ID NO 26
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 26

Thr Arg Ala Glu Ile Glu Asp Glu Leu Ile Arg Ala Asp Ile Glu Ser
1               5                   10                  15

Asn Pro Gly Pro
            20

<210> SEQ ID NO 27
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 27

Ala Lys Phe Gln Ile Asp Lys Ile Leu Ile Ser Gly Asp Val Glu Leu
1               5                   10                  15

Asn Pro Gly Pro
            20

<210> SEQ ID NO 28
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 28

Ser Ser Ile Ile Arg Thr Lys Met Leu Val Ser Gly Asp Val Glu Glu
1               5                   10                  15

Asn Pro Gly Pro
            20

<210> SEQ ID NO 29
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 29

```
Cys Asp Ala Gln Arg Gln Lys Leu Leu Leu Ser Gly Asp Ile Glu Gln
1               5                   10                  15

Asn Pro Gly Pro
            20

<210> SEQ ID NO 30
<211> LENGTH: 20
<212> TYPE: PRT
<213> ORGANISM: Artificial Sequence
<220> FEATURE:
<223> OTHER INFORMATION: 2A-like self-cleaving peptide

<400> SEQUENCE: 30

Tyr Pro Ile Asp Phe Gly Gly Phe Leu Val Lys Ala Asp Ser Glu Phe
1               5                   10                  15

Asn Pro Gly Pro
            20

<210> SEQ ID NO 31
<211> LENGTH: 57
<212> TYPE: PRT
<213> ORGANISM: Artificial Sequence
<220> FEATURE:
<223> OTHER INFORMATION: Self-cleaving peptide

<400> SEQUENCE: 31

Val Thr Glu Leu Leu Tyr Arg Met Lys Arg Ala Glu Thr Tyr Cys Pro
1               5                   10                  15

Arg Pro Leu Ala Ile His Pro Thr Glu Ala Arg His Lys Gln Lys Ile
                20                  25                  30

Val Ala Pro Val Lys Gln Thr Leu Asn Phe Asp Leu Leu Lys Leu Ala
            35                  40                  45

Gly Asp Val Glu Ser Asn Pro Gly Pro
        50                  55

<210> SEQ ID NO 32
<211> LENGTH: 40
<212> TYPE: PRT
<213> ORGANISM: Artificial Sequence
<220> FEATURE:
<223> OTHER INFORMATION: Self-cleaving peptide

<400> SEQUENCE: 32

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
                20                  25                  30

Asp Val Glu Ser Asn Pro Gly Pro
            35                  40

<210> SEQ ID NO 33
<211> LENGTH: 33
<212> TYPE: PRT
<213> ORGANISM: Artificial Sequence
<220> FEATURE:
<223> OTHER INFORMATION: Self-cleaving peptide

<400> SEQUENCE: 33

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
                20                  25                  30
```

Pro

<210> SEQ ID NO 34
<211> LENGTH: 24
<212> TYPE: PRT
<213> ORGANISM: Artificial Sequence
<220> FEATURE:
<223> OTHER INFORMATION: Self-cleaving peptide

<400> SEQUENCE: 34

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 35
<211> LENGTH: 20
<212> TYPE: PRT
<213> ORGANISM: Mus musculus

<400> SEQUENCE: 35

Met Glu Thr Asp Thr Leu Ile Leu Trp Val Leu Leu Leu Leu Val Pro
1               5                   10                  15

Gly Ser Thr Gly
            20

<210> SEQ ID NO 36
<211> LENGTH: 25
<212> TYPE: PRT
<213> ORGANISM: Artificial Sequence
<220> FEATURE:
<223> OTHER INFORMATION: Signal peptide, T-cell surface glycoprotein
      CD4

<400> SEQUENCE: 36

Met Asn Arg Gly Val Pro Phe Arg His Leu Leu Leu Val Leu Gln Leu
1               5                   10                  15

Ala Leu Leu Pro Ala Ala Thr Gln Gly
            20                  25

<210> SEQ ID NO 37
<211> LENGTH: 23
<212> TYPE: PRT
<213> ORGANISM: Artificial Sequence
<220> FEATURE:
<223> OTHER INFORMATION: Signal peptide, leukocyte common antigen

<400> SEQUENCE: 37

Met Tyr Leu Trp Leu Lys Leu Leu Ala Phe Gly Phe Ala Phe Leu Asp
1               5                   10                  15

Thr Glu Val Phe Val Thr Gly
            20

<210> SEQ ID NO 38
<211> LENGTH: 21
<212> TYPE: PRT
<213> ORGANISM: Artificial Sequence
<220> FEATURE:
<223> OTHER INFORMATION: Signal peptide, T-cell surface glycoprotein CD8
      alpha chain

<400> SEQUENCE: 38

Met Ala Leu Pro Val Thr Ala Leu Leu Leu Pro Leu Ala Leu Leu Leu
1               5                   10                  15

His Ala Ala Arg Pro
            20

<210> SEQ ID NO 39
<211> LENGTH: 21
<212> TYPE: PRT
<213> ORGANISM: Artificial Sequence
<220> FEATURE:
<223> OTHER INFORMATION: Signal peptide, T-cell surface glycoprotein CD8
      beta chain

<400> SEQUENCE: 39

Met Arg Pro Arg Leu Trp Leu Leu Leu Ala Ala Gln Leu Thr Val Leu
1               5                   10                  15

His Gly Asn Ser Val
            20

<210> SEQ ID NO 40
<211> LENGTH: 24
<212> TYPE: PRT
<213> ORGANISM: Artificial Sequence
<220> FEATURE:
<223> OTHER INFORMATION: Signal peptide, T-cell surface antigen CD2

<400> SEQUENCE: 40

Met Ser Phe Pro Cys Lys Phe Val Ala Ser Phe Leu Leu Ile Phe Asn
1               5                   10                  15

Val Ser Ser Lys Gly Ala Val Ser
            20

<210> SEQ ID NO 41
<211> LENGTH: 24
<212> TYPE: PRT
<213> ORGANISM: Artificial Sequence
<220> FEATURE:
<223> OTHER INFORMATION: Signal peptide, T-cell surface glycoprotein CD5

<400> SEQUENCE: 41

Met Pro Met Gly Ser Leu Gln Pro Leu Ala Thr Leu Tyr Leu Leu Gly
1               5                   10                  15

Met Leu Val Ala Ser Cys Leu Gly
            20

<210> SEQ ID NO 42
<211> LENGTH: 25
<212> TYPE: PRT
<213> ORGANISM: Artificial Sequence
<220> FEATURE:
<223> OTHER INFORMATION: Signal peptide, T-cell antigen CD7

<400> SEQUENCE: 42

Met Ala Gly Pro Pro Arg Leu Leu Leu Leu Pro Leu Leu Leu Ala Leu
1               5                   10                  15

Ala Arg Gly Leu Pro Gly Ala Leu Ala
            20                  25

<210> SEQ ID NO 43
<211> LENGTH: 24
<212> TYPE: PRT
<213> ORGANISM: Artificial Sequence
<220> FEATURE:
<223> OTHER INFORMATION: Signal peptide, 5,6-dihydroxyindole-2-
      carboxylic acid oxidase

<400> SEQUENCE: 43

```
Met Ser Ala Pro Lys Leu Leu Ser Leu Gly Cys Ile Phe Phe Pro Leu
1               5                   10                  15

Leu Leu Phe Gln Gln Ala Arg Ala
            20

<210> SEQ ID NO 44
<211> LENGTH: 19
<212> TYPE: PRT
<213> ORGANISM: Artificial Sequence
<220> FEATURE:
<223> OTHER INFORMATION: Signal peptide, alpha-lactalbumin

<400> SEQUENCE: 44

Met Arg Phe Phe Val Pro Leu Phe Leu Val Gly Ile Leu Phe Pro Ala
1               5                   10                  15

Ile Leu Ala

<210> SEQ ID NO 45
<211> LENGTH: 23
<212> TYPE: PRT
<213> ORGANISM: Artificial Sequence
<220> FEATURE:
<223> OTHER INFORMATION: Signal peptide, beta-galactosidase

<400> SEQUENCE: 45

Met Pro Gly Phe Leu Val Arg Ile Leu Pro Leu Leu Leu Val Leu Leu
1               5                   10                  15

Leu Leu Gly Pro Thr Arg Gly
            20

<210> SEQ ID NO 46
<211> LENGTH: 24
<212> TYPE: PRT
<213> ORGANISM: Artificial Sequence
<220> FEATURE:
<223> OTHER INFORMATION: Signal peptide, CAMPATH-1 antigen

<400> SEQUENCE: 46

Met Lys Arg Phe Leu Phe Leu Leu Leu Thr Ile Ser Leu Leu Val Met
1               5                   10                  15

Val Gln Ile Gln Thr Gly Leu Ser
            20

<210> SEQ ID NO 47
<211> LENGTH: 21
<212> TYPE: PRT
<213> ORGANISM: Artificial Sequence
<220> FEATURE:
<223> OTHER INFORMATION: Signal peptide, CD109 antigen

<400> SEQUENCE: 47

Met Gln Gly Pro Pro Leu Leu Thr Ala Ala His Leu Leu Cys Val Cys
1               5                   10                  15

Thr Ala Ala Leu Ala
            20

<210> SEQ ID NO 48
<211> LENGTH: 22
<212> TYPE: PRT
<213> ORGANISM: Artificial Sequence
<220> FEATURE:
<223> OTHER INFORMATION: Signal peptide, Complement C3

<400> SEQUENCE: 48
```

Met Gly Pro Thr Ser Gly Pro Ser Leu Leu Leu Leu Leu Thr His
1               5                   10                  15

Leu Pro Leu Ala Leu Gly
            20

<210> SEQ ID NO 49
<211> LENGTH: 18
<212> TYPE: PRT
<213> ORGANISM: Artificial Sequence
<220> FEATURE:
<223> OTHER INFORMATION: Signal peptide, Granzyme B

<400> SEQUENCE: 49

Met Gln Pro Ile Leu Leu Leu Leu Ala Phe Leu Leu Leu Pro Arg Ala
1               5                   10                  15

Asp Ala

<210> SEQ ID NO 50
<211> LENGTH: 20
<212> TYPE: PRT
<213> ORGANISM: Artificial Sequence
<220> FEATURE:
<223> OTHER INFORMATION: Signal peptide, Ig kappa chain V-III region VH

<400> SEQUENCE: 50

Met Glu Ala Pro Ala Gln Leu Leu Phe Leu Leu Leu Leu Trp Leu Pro
1               5                   10                  15

Asp Thr Thr Arg
            20

<210> SEQ ID NO 51
<211> LENGTH: 20
<212> TYPE: PRT
<213> ORGANISM: Artificial Sequence
<220> FEATURE:
<223> OTHER INFORMATION: Signal peptide, Ig kappa chain V-IV region

<400> SEQUENCE: 51

Met Val Leu Gln Thr Gln Val Phe Ile Ser Leu Leu Leu Trp Ile Ser
1               5                   10                  15

Gly Ala Tyr Gly
            20

<210> SEQ ID NO 52
<211> LENGTH: 19
<212> TYPE: PRT
<213> ORGANISM: Artificial Sequence
<220> FEATURE:
<223> OTHER INFORMATION: Signal peptide, Ig lambda chain V-VI region EB4

<400> SEQUENCE: 52

Met Ala Trp Ala Pro Leu Leu Leu Thr Leu Leu Ala His Cys Thr Asp
1               5                   10                  15

Cys Trp Ala

<210> SEQ ID NO 53
<211> LENGTH: 22
<212> TYPE: PRT
<213> ORGANISM: Artificial Sequence
<220> FEATURE:
<223> OTHER INFORMATION: Signal peptide, cytokine receptor common gamma
      chain

<400> SEQUENCE: 53

```
Met Leu Lys Pro Ser Leu Pro Phe Thr Ser Leu Leu Phe Leu Gln Leu
1               5                   10                  15

Pro Leu Leu Gly Val Gly
            20

<210> SEQ ID NO 54
<211> LENGTH: 20
<212> TYPE: PRT
<213> ORGANISM: Artificial Sequence
<220> FEATURE:
<223> OTHER INFORMATION: Signal peptide, bactericidal/permeability-
      increasing protein-like 1

<400> SEQUENCE: 54

Met Ala Trp Ala Ser Arg Leu Gly Leu Leu Ala Leu Leu Leu Pro
1               5                   10                  15

Val Val Gly Ala
            20

<210> SEQ ID NO 55
<211> LENGTH: 23
<212> TYPE: PRT
<213> ORGANISM: Artificial Sequence
<220> FEATURE:
<223> OTHER INFORMATION: Signal peptide, IgG receptor FcRn large subunit
      p51

<400> SEQUENCE: 55

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 56
<211> LENGTH: 248
<212> TYPE: PRT
<213> ORGANISM: Artificial Sequence
<220> FEATURE:
<223> OTHER INFORMATION: scFv aCD19, chimeric antigen receptor (CAR)
      sequence

<400> SEQUENCE: 56

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Lys Ala Gly Gly Gly
            100                 105                 110

Gly Ser Gly Gly Gly Gly Ser Gly Gly Gly Gly Ser Gly Gly Gly Gly
        115                 120                 125

Ser Glu Val Lys Leu Gln Glu Ser Gly Pro Gly Leu Val Ala Pro Ser
    130                 135                 140
```

```
Gln Ser Leu Ser Val Thr Cys Thr Val Ser Gly Val Ser Leu Pro Asp
145                 150                 155                 160

Tyr Gly Val Ser Trp Ile Arg Gln Pro Pro Arg Lys Gly Leu Glu Trp
            165                 170                 175

Leu Gly Val Ile Trp Gly Ser Glu Thr Thr Tyr Tyr Asn Ser Ala Leu
            180                 185                 190

Lys Ser Arg Leu Thr Ile Ile Lys Asp Asn Ser Lys Ser Gln Val Phe
            195                 200                 205

Leu Lys Met Asn Ser Leu Gln Thr Asp Asp Thr Ala Ile Tyr Tyr Cys
            210                 215                 220

Ala Lys His Tyr Tyr Tyr Gly Gly Ser Tyr Ala Met Asp Tyr Trp Gly
225                 230                 235                 240

Gln Gly Thr Ser Val Thr Val Ser
            245
```

<210> SEQ ID NO 57
<211> LENGTH: 47
<212> TYPE: PRT
<213> ORGANISM: Artificial Sequence
<220> FEATURE:
<223> OTHER INFORMATION: Human CD8aSTK

<400> SEQUENCE: 57

```
Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp Ile
        35                  40                  45
```

<210> SEQ ID NO 58
<211> LENGTH: 27
<212> TYPE: PRT
<213> ORGANISM: Artificial Sequence
<220> FEATURE:
<223> OTHER INFORMATION: Human CD28TM

<400> SEQUENCE: 58

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 59
<211> LENGTH: 113
<212> TYPE: PRT
<213> ORGANISM: Artificial Sequence
<220> FEATURE:
<223> OTHER INFORMATION: Human CD3zeta intracellular domain

<400> SEQUENCE: 59

```
Arg Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
```

```
                65                  70                  75                  80
Arg Arg Arg Gly Lys Gly His Asp Gly Leu Tyr Gln Gly Leu Ser Thr
                    85                  90                  95
Ala Thr Lys Asp Thr Tyr Asp Ala Leu His Met Gln Ala Leu Pro Pro
                    100                 105                 110
Arg

<210> SEQ ID NO 60
<211> LENGTH: 20
<212> TYPE: PRT
<213> ORGANISM: Artificial Sequence
<220> FEATURE:
<223> OTHER INFORMATION: 2A self-cleaving peptide

<400> SEQUENCE: 60

Arg Ala Glu Gly Arg Gly Ser Leu Leu Thr Cys Gly Asp Val Glu Glu
1               5                   10                  15

Asn Pro Gly Pro
            20

<210> SEQ ID NO 61
<211> LENGTH: 18
<212> TYPE: PRT
<213> ORGANISM: Artificial Sequence
<220> FEATURE:
<223> OTHER INFORMATION: Signal peptide derived from mouse Ig kappa

<400> SEQUENCE: 61

Met Ala Val Pro Thr Gln Val Leu Gly Leu Leu Leu Leu Trp Leu Thr
1               5                   10                  15

Asp Ala

<210> SEQ ID NO 62
<211> LENGTH: 254
<212> TYPE: PRT
<213> ORGANISM: Artificial Sequence
<220> FEATURE:
<223> OTHER INFORMATION: scFv aCD33, chimeric antigen receptor (CAR)
      sequence

<400> SEQUENCE: 62

Arg Cys Asp Ile Gln Met Thr Gln Ser Pro Ser Ser Leu Ser Ala Ser
1               5                   10                  15

Val Gly Asp Arg Val Thr Ile Thr Cys Arg Ala Ser Glu Asp Ile Tyr
            20                  25                  30

Phe Asn Leu Val Trp Tyr Gln Gln Lys Pro Gly Lys Ala Pro Lys Leu
        35                  40                  45

Leu Ile Tyr Asp Thr Asn Arg Leu Ala Asp Gly Val Pro Ser Arg Phe
    50                  55                  60

Ser Gly Ser Gly Ser Gly Thr Gln Tyr Thr Leu Thr Ile Ser Ser Leu
65                  70                  75                  80

Gln Pro Glu Asp Phe Ala Thr Tyr Tyr Cys Gln His Tyr Lys Asn Tyr
                85                  90                  95

Pro Leu Thr Phe Gly Gln Gly Thr Lys Leu Glu Ile Lys Arg Ser Gly
            100                 105                 110

Gly Gly Gly Ser Gly Gly Gly Gly Ser Gly Gly Gly Gly Ser Gly Gly
        115                 120                 125

Gly Gly Ser Arg Ser Glu Val Gln Leu Val Glu Ser Gly Gly Gly Leu
    130                 135                 140
```

Val Gln Pro Gly Gly Ser Leu Arg Leu Ser Cys Ala Ala Ser Gly Phe
145                 150                 155                 160

Thr Leu Ser Asn Tyr Gly Met His Trp Ile Arg Gln Ala Pro Gly Lys
            165                 170                 175

Gly Leu Glu Trp Val Ser Ser Ile Ser Leu Asn Gly Gly Ser Thr Tyr
            180                 185                 190

Tyr Arg Asp Ser Val Lys Gly Arg Phe Thr Ile Ser Arg Asp Asn Ala
            195                 200                 205

Lys Ser Thr Leu Tyr Leu Gln Met Asn Ser Leu Arg Ala Glu Asp Thr
            210                 215                 220

Ala Val Tyr Tyr Cys Ala Ala Gln Asp Ala Tyr Thr Gly Gly Tyr Phe
225                 230                 235                 240

Asp Tyr Trp Gly Gln Gly Thr Leu Val Thr Val Ser Ser Met
            245                 250

<210> SEQ ID NO 63
<211> LENGTH: 231
<212> TYPE: PRT
<213> ORGANISM: Artificial Sequence
<220> FEATURE:
<223> OTHER INFORMATION: Hinge and Fc derived from human IgG1 with
      mutations to prevent FcRg association (HCH2CH3pvaa)

<400> SEQUENCE: 63

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
            85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
            165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 64

-continued

```
<211> LENGTH: 4
<212> TYPE: PRT
<213> ORGANISM: Artificial Sequence
<220> FEATURE:
<223> OTHER INFORMATION: Linker

<400> SEQUENCE: 64

Lys Asp Pro Lys
1

<210> SEQ ID NO 65
<211> LENGTH: 21
<212> TYPE: PRT
<213> ORGANISM: Artificial Sequence
<220> FEATURE:
<223> OTHER INFORMATION: Human CD148TM

<400> SEQUENCE: 65

Ala Val Phe Gly Cys Ile Phe Gly Ala Leu Val Ile Val Thr Val Gly
1               5                   10                  15

Gly Phe Ile Phe Trp
            20

<210> SEQ ID NO 66
<211> LENGTH: 341
<212> TYPE: PRT
<213> ORGANISM: Artificial Sequence
<220> FEATURE:
<223> OTHER INFORMATION: Human CD148 intracellular domain

<400> SEQUENCE: 66

Arg Lys Lys Arg Lys Asp Ala Lys Asn Asn Glu Val Ser Phe Ser Gln
1               5                   10                  15

Ile Lys Pro Lys Lys Ser Lys Leu Ile Arg Val Glu Asn Phe Glu Ala
            20                  25                  30

Tyr Phe Lys Lys Gln Gln Ala Asp Ser Asn Cys Gly Phe Ala Glu Glu
        35                  40                  45

Tyr Glu Asp Leu Lys Leu Val Gly Ile Ser Gln Pro Lys Tyr Ala Ala
    50                  55                  60

Glu Leu Ala Glu Asn Arg Gly Lys Asn Arg Tyr Asn Asn Val Leu Pro
65                  70                  75                  80

Tyr Asp Ile Ser Arg Val Lys Leu Ser Val Gln Thr His Ser Thr Asp
                85                  90                  95

Asp Tyr Ile Asn Ala Asn Tyr Met Pro Gly Tyr His Ser Lys Lys Asp
            100                 105                 110

Phe Ile Ala Thr Gln Gly Pro Leu Pro Asn Thr Leu Lys Asp Phe Trp
        115                 120                 125

Arg Met Val Trp Glu Lys Asn Val Tyr Ala Ile Ile Met Leu Thr Lys
    130                 135                 140

Cys Val Glu Gln Gly Arg Thr Lys Cys Glu Glu Tyr Trp Pro Ser Lys
145                 150                 155                 160

Gln Ala Gln Asp Tyr Gly Asp Ile Thr Val Ala Met Thr Ser Glu Ile
                165                 170                 175

Val Leu Pro Glu Trp Thr Ile Arg Asp Phe Thr Val Lys Asn Ile Gln
            180                 185                 190

Thr Ser Glu Ser His Pro Leu Arg Gln Phe His Phe Thr Ser Trp Pro
        195                 200                 205

Asp His Gly Val Pro Asp Thr Thr Asp Leu Leu Ile Asn Phe Arg Tyr
    210                 215                 220
```

```
Leu Val Arg Asp Tyr Met Lys Gln Ser Pro Pro Glu Ser Pro Ile Leu
225                 230                 235                 240

Val His Cys Ser Ala Gly Val Gly Arg Thr Gly Thr Phe Ile Ala Ile
                245                 250                 255

Asp Arg Leu Ile Tyr Gln Ile Glu Asn Glu Asn Thr Val Asp Val Tyr
                260                 265                 270

Gly Ile Val Tyr Asp Leu Arg Met His Arg Pro Leu Met Val Gln Thr
            275                 280                 285

Glu Asp Gln Tyr Val Phe Leu Asn Gln Cys Val Leu Asp Ile Val Arg
        290                 295                 300

Ser Gln Lys Asp Ser Lys Val Asp Leu Ile Tyr Gln Asn Thr Thr Ala
305                 310                 315                 320

Met Thr Ile Tyr Glu Asn Leu Ala Pro Val Thr Thr Phe Gly Lys Thr
                325                 330                 335

Asn Gly Tyr Ile Ala
            340

<210> SEQ ID NO 67
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: MISC_FEATURE
<222> LOCATION: (2)..(2)
<223> OTHER INFORMATION: Xaa can be any naturally occuring amino acid

<400> SEQUENCE: 67

Arg Xaa Arg Arg
1

<210> SEQ ID NO 68
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: MISC_FEATURE
<222> LOCATION: (2)..(2)
<223> OTHER INFORMATION: Xaa can be any naturally occuring amino acid

<400> SEQUENCE: 68

Arg Xaa Lys Arg
1

<210> SEQ ID NO 69
<211> LENGTH: 7
<212> TYPE: PRT
<213> ORGANISM: Artificial Sequence
<220> FEATURE:
<223> OTHER INFORMATION: Tobacco Etch Virus (TEV) cleavage site

<400> SEQUENCE: 69

Glu Asn Leu Tyr Phe Gln Ser
1               5

<210> SEQ ID NO 70
<211> LENGTH: 8
<212> TYPE: PRT
<213> ORGANISM: Artificial Sequence
<220> FEATURE:
<223> OTHER INFORMATION: Cleavage site motif
<220> FEATURE:
```

```
<221> NAME/KEY: MISC_FEATURE
<222> LOCATION: (2)..(2)
<223> OTHER INFORMATION: Xaa can be any naturally occuring amino acid
<220> FEATURE:
<221> NAME/KEY: MISC_FEATURE
<222> LOCATION: (4)..(4)
<223> OTHER INFORMATION: Xaa can be any naturally occuring amino acid

<400> SEQUENCE: 70

Asp Xaa Glu Xaa Asn Pro Gly Pro
1               5

<210> SEQ ID NO 71
<211> LENGTH: 8
<212> TYPE: PRT
<213> ORGANISM: Artificial Sequence
<220> FEATURE:
<223> OTHER INFORMATION: Cleavage site motif
<220> FEATURE:
<221> NAME/KEY: MISC_FEATURE
<222> LOCATION: (2)..(2)
<223> OTHER INFORMATION: Xaa may be ILE,VAL, MET or SER
<220> FEATURE:
<221> NAME/KEY: MISC_FEATURE
<222> LOCATION: (4)..(4)
<223> OTHER INFORMATION: Xaa may be THR, MET, SER, LEU, GLU, GLN or PHE

<400> SEQUENCE: 71

Asp Xaa Glu Xaa Asn Pro Gly Pro
1               5

<210> SEQ ID NO 72
<211> LENGTH: 4
<212> TYPE: PRT
<213> ORGANISM: Mus musculus

<400> SEQUENCE: 72

Met Glu Thr Asp
1

<210> SEQ ID NO 73
<211> LENGTH: 11
<212> TYPE: PRT
<213> ORGANISM: Mus musculus

<400> SEQUENCE: 73

Thr Leu Ile Leu Trp Val Leu Leu Leu Leu Val
1               5                   10

<210> SEQ ID NO 74
<211> LENGTH: 5
<212> TYPE: PRT
<213> ORGANISM: Mus musculus

<400> SEQUENCE: 74

Pro Gly Ser Thr Gly
1               5
```